US011633135B2

(12) United States Patent
Bashan et al.

(10) Patent No.: US 11,633,135 B2
(45) Date of Patent: Apr. 25, 2023

(54) DEVICE, SYSTEM AND METHOD FOR CALIBRATING A NON-INVASIVE HEALTH MONITORING DEVICE

(71) Applicant: Wear2B Ltd., Rosh Pina (IL)

(72) Inventors: Ohad Bashan, Sde Varburg (IL); Oded Bashan, Rosh Pina (IL); Aharon Klein, Haifa (IL); Ben Zion Dekel, Hadera (IL); Giora Bar-Sakai, Tel Aviv (IL)

(73) Assignee: WEAR2B LTD., Rosh Pina (IL)

( * ) Notice: Subject to any disclaimer, the term of this patent is extended or adjusted under 35 U.S.C. 154(b) by 961 days.

(21) Appl. No.: 16/339,403

(22) PCT Filed: Oct. 2, 2017

(86) PCT No.: PCT/IL2017/051115
§ 371 (c)(1),
(2) Date: Apr. 4, 2019

(87) PCT Pub. No.: WO2018/065981
PCT Pub. Date: Apr. 12, 2018

(65) Prior Publication Data
US 2020/0037933 A1 Feb. 6, 2020

Related U.S. Application Data

(60) Provisional application No. 62/404,813, filed on Oct. 6, 2016.

(51) Int. Cl.
*A61B 5/1495* (2006.01)
*A61B 5/145* (2006.01)
(Continued)

(52) U.S. Cl.
CPC .......... *A61B 5/1495* (2013.01); *A61B 5/1455* (2013.01); *A61B 5/14546* (2013.01);
(Continued)

(58) Field of Classification Search
CPC . A61B 5/1495; A61B 5/14546; A61B 5/1455; A61B 5/14532; G01N 21/274; G01N 21/4785
See application file for complete search history.

(56) References Cited

U.S. PATENT DOCUMENTS 6,196,046 B1 * 3/2001 Braig ................... A61B 5/1495
73/1.03
6,456,870 B1 9/2002 Rennert et al.
(Continued)

FOREIGN PATENT DOCUMENTS

JP 2003-507732 2/2003
JP 2007-259967 10/2007
(Continued)

OTHER PUBLICATIONS

International Search Report of Application No. PCT/IL2017/051115 dated Jan. 25, 2018.
Supplementary European Search Report for European App. No. 17857972 dated May 19, 2020.
Office Action from Japanese Application No. 2019-518309, dated Aug. 3, 2021.

*Primary Examiner* — Dominic J Bologna
(74) *Attorney, Agent, or Firm* — Pearl Cohen Zedek Latzer Baratz LLP (57) ABSTRACT

A system for calibrating a device for measuring materials concentration in the blood is disclosed. The system may include at least two sets of calibrating elements, each set may include a plurality of calibrating elements. Each of the calibrating elements in the sets may include, a first layer simulating a specific human skin characteristics; and a second layer consisting a specific concentration of one or more materials in the blood. For all calibrating elements in a set the first layer may be the same first layer simulating the same human skin characteristics such that each set of calibrating elements simulate different skin characteristics. Each calibrating element in a set of calibrating elements may (Continued)

include a different second layer consisting a different concentration of the one or more materials. The system may further include a controller.

6 Claims, 4 Drawing Sheets

(51) Int. Cl.
*A61B 5/1455* (2006.01)
*G01N 21/27* (2006.01)
*G01N 21/47* (2006.01)

(52) U.S. Cl.
CPC ....... *G01N 21/274* (2013.01); *G01N 21/4785* (2013.01); *A61B 5/14532* (2013.01)

(56) References Cited

U.S. PATENT DOCUMENTS

| | | | |
|---|---|---|---|
| 7,899,636 B2 | 3/2011 | Bakker | |
| 2002/0133080 A1* | 9/2002 | Apruzzese | G01N 21/6486 |
| | | | 600/477 |
| 2010/0042348 A1* | 2/2010 | Bakker | G01N 21/65 |
| | | | 356/243.1 |
| 2012/0095305 A1 | 4/2012 | Wang et al. | |
| 2014/0298886 A1 | 10/2014 | Nishi | |
| 2016/0097716 A1 | 4/2016 | Gulati et al. | |

FOREIGN PATENT DOCUMENTS

| | | |
|---|---|---|
| JP | 2016-150130 | 8/2016 |
| RU | 2398232 | 10/2010 |
| WO | WO 01/14848 | 3/2001 |

\* cited by examiner

DEVICE, SYSTEM AND METHOD FOR CALIBRATING A NON-INVASIVE HEALTH MONITORING DEVICE

CROSS-REFERENCE TO RELATED APPLICATIONS

This application is a National Phase Application of PCT International Application No. PCT/IL2017/051115, International Filing Date Oct. 2, 2017, claiming the benefit of U.S. Patent Application No. 62/404,813, filed Oct. 6, 2016, which is hereby incorporated by reference.

BACKGROUND OF THE INVENTION

Noninvasive blood test measurements are the future of blood measurements. They are simple, harmless, unpainful and do not involve laboratory time. Several commercial products for noninvasive measurements are available today. However, for these devices to work properly they must be accurately calibrated to suit specific patients.

Noninvasive blood test measurements are performed by attaching a measurement device to the patient's skin. These devices are usually operated by sending electromagnetic signals (e.g., visual light, IR radiation, RF radiation, etc.) via the patient skin targeting a blood vessel and reading reflection received from the blood vessel. Different humans' skin has different characteristics, such as, different thicknesses of different skin layers, different amount of hair, different amount of pigment etc., and therefore may absorb differently the electromagnetic signals sent from the noninvasive measurements device. Accordingly, there is a need for a noninvasive blood measurement deceive that may be calibrated specifically to each user so to measure accurately, concentrations of various materials in the blood for patients with different skin characteristics and different anatomy.

SUMMARY

Some aspects of the invention are directed to a system for calibrating a device for measuring materials concentration in the blood. The system may include at least two sets of calibrating elements, each set comprising a plurality of calibrating elements. In some embodiments, each of the calibrating elements may include, a first layer simulating a specific human skin characteristics; and a second layer consisting a specific concentration of one or more materials in the blood. In some embodiments, all calibrating elements in a set the first layer may be the same first layer simulating the same human skin characteristics such that each set of calibrating elements simulate different skin characteristics. In some embodiments, each calibrating element in a set of calibrating elements may include a different second layer consisting a different concentration of the one or more material. In some embodiments, the system may further include a controller that may be configured to: receive illumination intensities from the device for measuring materials concentration when the device is attached to each calibrating element of the system; associate the received illumination intensities with the specific skin characteristics and the specific concentration of the calibrating element to which the device is attached; and save the illumination intensities associated with the specific skin characteristics and the specific concentration in lookup tables in a memory of the device for measuring materials concentration.

In some embodiments, the skin characteristic may be at least one of: skin thickness, skin color, skin hair density, skin tone, skin temperature, skin optical properties and skin hair color. In some embodiments, the received illumination intensities may include illumination intensities at various wavelengths and the saved lookup tables include lookup tables for illumination intensities of a specific wavelength associated with the specific skin characteristics, the one or more materials and the specific concentration. In some embodiments, the system may further include a third layer for simulating illumination reflection from a blood vessel in a skin tissue.

Some other aspects of the invention may be related to a system for calibrating a device for measuring materials concentration in the blood. The system may include a first sets of calibrating elements and a second set of calibrating elements. In some embodiments, each of the calibrating elements in the first and second sets may include a first layer simulating a specific human skin characteristic; and a second layer consisting a specific concentration of one or more materials in the blood, such that in the first set of calibrating elements the first layer simulates a first human skin characteristic and in the second set of calibrating elements the first layer simulates a second human skin characteristic, different from the first human skin characteristic. In some embodiments, wherein each calibrating element in the first set may include a different second layer consisting a different concentration of the one or more materials, and each calibrating element in the second set may include a different second layer consisting a different concentration of the one or more materials. In some embodiments, the system may further include a controller that may be configured to: receive illumination intensities from the device for measuring materials concentration when the device is attached to each calibrating element of the system; associate the received illumination intensities with the specific skin characteristic and the specific concentration of the measured one or more materials in the second layer of the calibrating element to which the device is attached; and save the illumination intensities associated with the specific skin thicknesses and the specific concentrations in a memory of the device for measuring materials concentration.

In some embodiments, the skin characteristic is at least one of: skin thickness, skin color, skin hair density, skin optical properties, and skin hair color.

Some additional aspects of the present invention may be related to a method of calibrating a device for measuring materials concentration in the blood. The method may include: attaching the device for measuring materials concentration to each calibrating element included in one of two or more sets of calibrating elements. In some embodiments, each of the calibrating elements may include: a first layer simulating a specific human skin characteristic; and a second layer consisting a specific concentration of one or more materials. In some embodiments, in all calibrating elements in a set the first layer may be the same first layer simulating the same human skin characteristic and each set of calibrating elements simulate different skin characteristic, and each calibrating element in a set of calibrating elements may include a different second layer consisting a different concentration of the one or more materials. In some embodiments, the method may further include: receiving, by a controller of a calibrating system, illumination intensities from the device for measuring materials concentration when the device is attached to each calibrating element; associating, by the controller, the received illumination intensities with the specific skin characteristic and the specific concentration of the one or more materials in the second layer of the calibrating element to which the device is attached; and recording, by the controller, the illumination intensities associated with the specific skin characteristic and the specific concentrations in a memory of the device for measuring materials concentration.

In some embodiments, receiving illumination intensities may include receiving illumination intensities at various wavelengths and recording the illumination intensities may include creating lookup tables for illumination intensities of a specific wavelength associated with the specific skin characteristic and the specific concentration.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the invention may be practiced without these specific details. In other instances, well-known methods, procedures, and components modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

Figure 1:
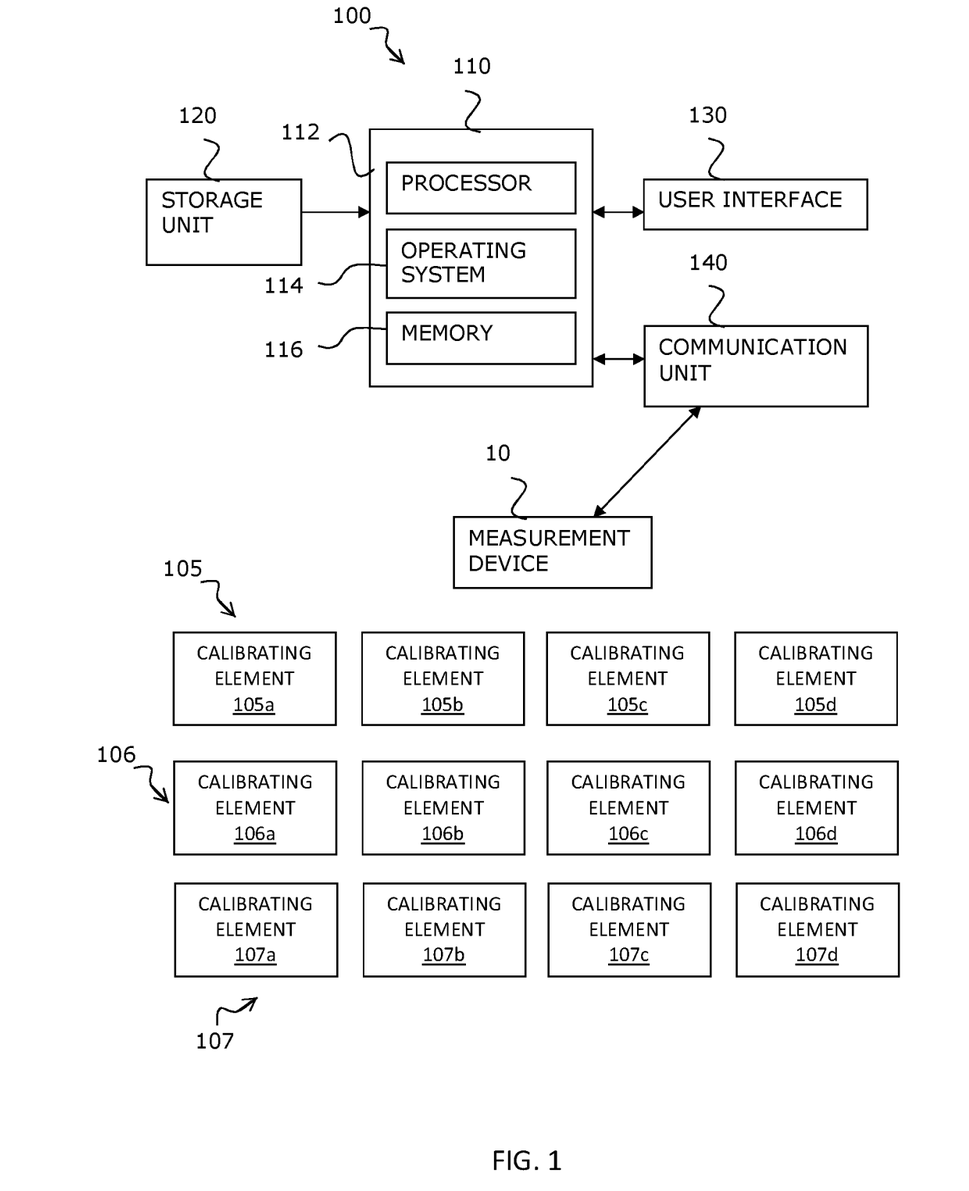
FIG. 1 is diagrammatic representation of a system for calibrating a device for measuring materials concentration in the blood according to some embodiments of the invention.

Reference is now made to FIG. 1 which is a diagrammatic representation of a system for calibrating a device for measuring materials concentration in the blood according to some embodiments of the invention. System 100 may include at least two sets 105 and 106 of calibrating elements 105a-105d and 106a-106d. In some embodiments, system 100 may include additional sets, for example, set 107, of calibrating elements 107a-107d. A detailed description of a calibrating element is given with respect to FIG. 3. System 100 may further include a controller 110, a storage unit 120 a user interface 130 and a communication unit 140. Communication unit 140 may be configured to send and receive information from a device 10 for measuring materials concentration in the blood.

In some embodiments, controller 110 may include a processor 112 that may be, for example, a central processing unit (CPU), a chip or any suitable computing or computational device, an operating system 114 and a memory 116. System 100 may include a desktop computer, laptop commuter, a tablet, a mainframe computer or the like. Processor 112 may be configured to carry out methods according to embodiments of the present invention by for example executing instructions stored in a memory such as memory 116.

Operating system 114 may be or may include any code segment designed and/or configured to perform tasks involving coordination, scheduling, arbitration, supervising, controlling or otherwise managing operation of controller 110, for example, scheduling execution of programs. Operating system 114 may be a commercial operating system. Memory 116 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 116 may be or may include a plurality of, possibly different memory units.

Memory 116 may store any executable code, e.g., an application, a program, a process, task or script. The executable code may include codes for calibrating a device for measuring materials concentration in the blood or any other codes or instruction for executing methods according to embodiments of the present invention. The executable code may be executed by processor 112 possibly under control of operating system 114.

Storage 120 may be or may include, for example, a hard disk drive, a floppy disk drive, a Compact Disk (CD) drive, a CD-Recordable (CD-R) drive, a universal serial bus (USB) device or other suitable removable and/or fixed storage unit. Content may be stored in storage 120 and may be loaded from storage 120 into memory 116 where it may be processed by processor 112. For example, storage 120 may include reference data related to measuring materials concentration in the blood, such as amplitude of reflected IR light in different wave lengths, representing: glucose blood levels, LDL (low density lipoproteins) levels in the blood, HDL (high density lipoprotein) levels in the blood, cholesterol levels in the blood, TG (Tri Glycerides) levels in the blood, Albumin levels in the blood, Hemoglobin levels in the blood, cardiac pulse frequency, cardiac pulse signal intensity, skin temp rate, body movement or lack of movement, body acceleration in different directions, horizontal positioning, skin thickness, skin pigmentation, User interface 130 may be or may include a screen, a pointing device and an audio device or any other device that may allow a user to send instructions and/or information to controller 110 and receive information from controller 110. For example, user interface 130 may include, a mouse, a touch screen or a pad, a keyboard, a microphone, speakers and the like.

In some embodiments, system 100 may further include a communication unit 140 for communication with at least one device 10 for measuring materials concentration in the blood. Communication unit 140 may include any applicable input/output (I/O) devices to connected controller 110 and device 10, for example, a wired or wireless network interface card (NIC), a modem, a universal serial bus (USB) device or external hard drive and the like.

Embodiments of the invention may include an article such as a computer or processor non-transitory readable medium, or a computer or processor non-transitory storage medium, such as for example a memory, a disk drive, or a USB flash memory, encoding, including or storing instructions, e.g., computer-executable instructions, which, when executed by a processor or controller, carry out methods disclosed herein.

The storage medium may include, but is not limited to, any type of disk including floppy disks, optical disks, compact disk read-only memories (CD-ROMs), rewritable compact disk (CD-RWs), and magneto-optical disks, semiconductor devices such as read-only memories (ROMs), random access memories (RAMs), such as a dynamic RAM (DRAM), erasable programmable read-only memories (EPROMs), flash memories, electrically erasable programmable read-only memories (EEPROMs), magnetic or optical cards, or any type of media suitable for storing electronic instructions, including programmable storage unit.

A system according to embodiments of the invention may include components such as, but not limited to, a plurality of central processing units (CPU) or any other suitable multipurpose or specific processors or controllers, a plurality of input units, a plurality of output units, a plurality of memory units, and a plurality of storage units. A system may additionally include other suitable hardware components and/or software components. In some embodiments, a system may include or may be, for example, a personal computer, a desktop computer, a mobile computer, a laptop computer, a notebook computer, a terminal, a workstation, a server computer, a tablet computer, a network device, or any other suitable computing device. Unless explicitly stated, the method embodiments described herein are not constrained to a particular order or sequence. Additionally, some of the described method embodiments or elements thereof can occur or be performed at the same point in time.

Figure 2:
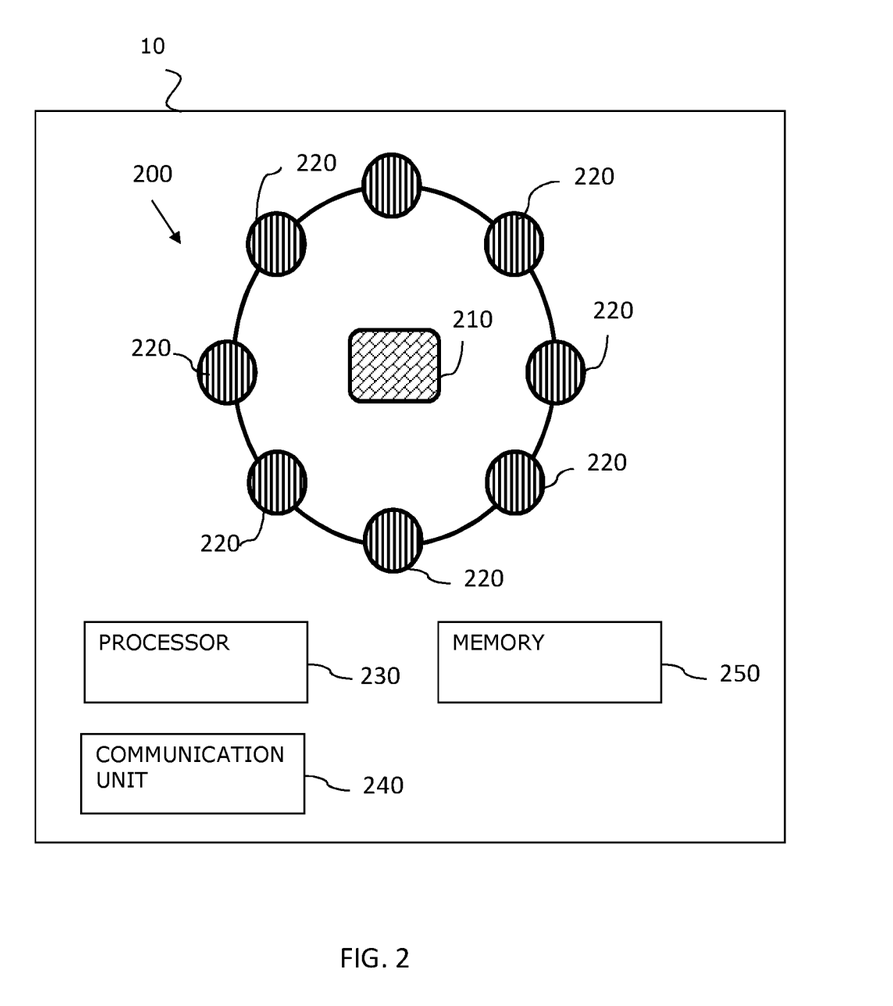
FIG. 2 is an illustration of a measurement device according to some embodiments of the invention.

Reference is now made to FIG. 2 which is an illustration of a device for measuring materials concentration in the blood according to some embodiments of the invention. Device 10 may be a wearable monitoring device configured to measure concentration of materials such as, glucose, albumin, insulin and the like, in a user's blood. Device 10 may include a measuring unit 200, a processor 230, a communication unit 240 and a memory 250. Measuring unit 200 may include at least one sensor 210 and at least one light emitting source 220. In some embodiments, measuring unit 200 may be adjacent to and in contact with the skin of a subject so as to reduce noise from the environment. It should be noted that with light emitted from the at least one light emitting source 220, device 10 may perform optical measurements that are noninvasive in contrast to commercially available invasive and minimal invasive solutions.

According to some embodiments, the EM radiation emitted from the at least one light emitting source 220, may be reflected from a subcutaneous tissue of the subject, and then detected by the at least one sensor 210 that may be, according to some embodiments, in the Infra-Red or near Infra-Red (IR) spectrum. For example, Short Wave IR (SWIR) imaging is utilized for measuring physiological signals from the blood of a subject. The SWIR waveband runs from the lower edge of the near IR region at 900 nm up to 2500 nm, and may be utilized for inspection of blood vessels in the body of the subject. It should be noted that if required, the range of the SWIR waveband may be increased.

It should be noted that device 10 may include measuring unit 200 in various configurations, and in some embodiments a single sensor 210 is surrounded by a plurality of light emitting sources 220 (as for example illustrated in FIG. 2). Other configuration may also employ a plurality of sensors 210 and light emitting sources.

In some embodiment, each light emitting source 220, or sub-sets (e.g. pairs, triplets etc.) of light emitting sources 220 may emit light in a different predetermined wavelength.

In some embodiment, each light emitting source 220, or sub-set of light emitting sources 220, may emit light in a different time and/or in a different frequency, such that not all light emitting sources 220 emit light simultaneously. This may provide additional information on the reflected tissue when the time intervals between the emissions of light beams are known.

According to some embodiments, the frequency of sampling by each light emitting source 220, or by each sub-set of light emitting sources 220, may be equal to or higher than Nyquist rate of the measured physiological signal.

In some non-limiting embodiments, polarized optical means may be utilized in order to increase the accuracy in the optical measurements. Specifically, emitting light beams with a predetermined polarization and receiving these beams with a substantially different polarization, for instance with dedicated filters, may improve the signal to noise ratio in the measurements. Furthermore, such polarizing may also provide improved indication on the penetration of the light beam into the tissue as noises from the external skin layer may be reduced while only signals from the beam reflected of the blood vessels is measured.

In some non-limiting embodiments, other sensors may also be utilized. For example acoustic ultrasound sensors, as well as terahertz sensors, RF sensors, microwave sensors and corresponding energy sources.

Figure 3:
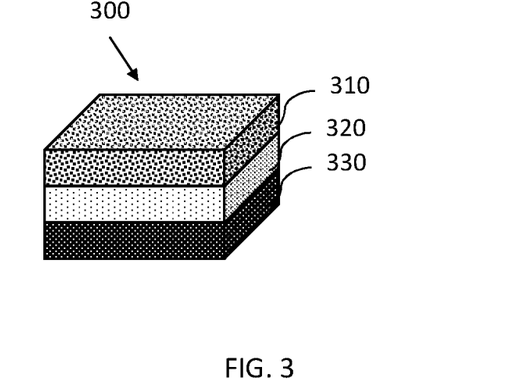
FIG. 3 is an illustration of a calibrating element according to some embodiments of the invention.

Reference is now made to FIG. 3 which is an illustration of a calibrating element according to some embodiments of the invention. A calibrating element 300 may include a first layer 310 simulating a specific human skin characteristics and a second layer 320 consisting a specific concentration of one or more materials in the blood, for example, glucose, albumin and insulin or a combination thereof. In some embodiments, the specific concentration may include specific concentrations of more than one material, for example, albumin and insulin. Skin characteristic according to embodiments of the invention may include at least one of:

skin thickness, skin temperature skin color, skin hair density, skin optical properties, and skin hair color. In some embodiments, the skin optical properties may include the ability of the skin to absorb, reflect and/or scattered EM radiation, for example, short wave infrared. The skin optical properties may include the scattering parameter (S-parameters) matrix.

In some embodiments, calibrating element 300 may further include a third layer 330 for simulating illumination reflection from a blood vessel in a skin tissue and for isolating the element from noise and reflections not related to the measured one or more materials in the second layer. Calibrating element 300 may include substantially the same types of layers as calibrating elements 105a-105d, 106a-106d and 107a-107b illustrated in FIG. 1. In some embodiments, calibrating element 300, 105a-105d, 106a-106d and 107a-107b may be configured to allow device 10 to be attached to the calibrating element in such a way that external light radiation does not interfere with the sent EM radiation and read EM reflections from the calibrating element. For example, calibrating element 300, 105a-105d, 106a-106d and 107a-107b may have a cylindrical shape to emulate the form of a human wrist or arm. Other shapes may be used.

First layer 310 may include any material that may simulate the EM absorption properties of the human skin. For example, first layer 310 may include materials that simulate melanin chromophores, skin proteins (collagen, elastin), water, blood lipids, hemoglobin or other blood components, that may simulate the reaction of a human skin to EM radiation emitted from one or more emitting sources 220. Some of calibration elements 300 may have different first layers simulating different skin characteristics. In some embodiments, sets 105, 106 and 107 may vary in the simulated thickness for example, elements 105a-105d may all have the same first layer simulating a skin thickness of 2 mm; elements 106a-106d may all have the same first layer simulating a skin thickness of 3 mm and elements 107a-107d may all have the same first layer simulated a skin thickness of 5 mm In some embodiments, system 100 of FIG. 1 may include sets having skin thicknesses of 2, 2.25, 2.5, 2.75, 3, 3.25 . . . 4.75 and 5 mm.

In some embodiments, at least some of the sets of calibrating elements may simulate different skin color & tone in addition to different skin thickness. For example, set 106 and set 107 may both simulate a skin thickness of 2.5 mm but with different amount of color pigment such as melanin chromophores, hemoglobin, other blood components, skin proteins (Elastin, collagen) etc.

Second layer 320 may include a liquid or solid solution comprising a specific concentration of one or more materials to be measured in the blood. For example, second layer 320 may include a specific concentration of albumin and/or glucose. In some embodiments, each calibrating element in a set of calibrating elements may include a different second layer having a different concentration of the one or more materials. For example, calibrating element 105a may include 3.5 g/dL of albumin, element 105b may include 3.6 g/dL of albumin, element 105c may include 3.7 g/dL of albumin and element 105d may include 3.8 g/dL of albumin. Similar or different albumin concentrations may be included in elements 106a-106d and 107a-107d. In yet another example, elements 106a-106d and 107a-107d may include different concentrations of albumin and glucose. It should be appreciated that while the example illustrated in FIG. 1 each set of elements 105, 106, 107 includes 4 calibration elements, any number of calibrating elements may be used in each set. Furthermore, it should be appreciated that according to some embodiments, different sets may have different number of calibrating elements.

Third layer 330 may include any material that will isolate and absorb the electromagnetic radiation emitted from one or more emitting source 220 the way a human organ/skin will do. For example, third layer 330 may include wood aluminum, metal, SWIR (short-wavelength infrared) opaque polymers and water.

Figure 4:
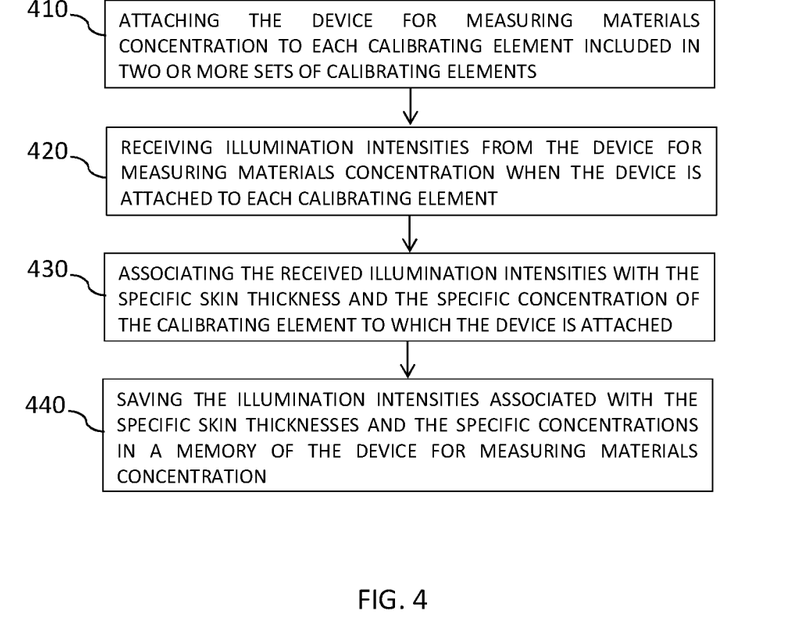
FIG. 4 is a flowchart of a method of calibrating a device for measuring materials concentration in the blood according to some embodiments of the invention.

Reference is now made to FIG. 4 which is a flowchart of a method of calibrating a device for measuring materials concentration in the blood according to some embodiments of the invention. The method of FIG. 4 may be performed using a system such as system 100. In operation 410, embodiments may include attaching the device for measuring materials concentration to each calibrating element included in two or more sets of calibrating elements. Device 10 may be attached, manually or automatically (e.g., by a robotic system) to at least some of the calibrating elements of system 100. For example, device 10 may be attached first to each of calibrating elements 105a-105d of set 105 and then be attached to each of calibrating elements 106a-106d of set 106, and so on.

In some embodiments, each time device 10 is being attached to a calibrating element, one or more light emitting sources 220 may emit EM radiation (e.g., light) into the calibrating element and one or more sensors 210 may read EM radiation reflected back from the calibrating element. Processor 230 may record in memory 250 the intensity (e.g., an optical value) at which the reflected EM radiation was sensed by one or more sensors 210. In some embodiments, one or more light emitting sources 220 may emit light at several wavelengths, for example, at 1100 nm and 1290 nm and sensor 210 may sense two different intensities (e.g., different optical values) for each wavelength. In some embodiments, processor 230 may be configured to send via communication unit 240 the recorded intensities to controller 110.

In operation 420, embodiments may include receiving illumination intensities from the device for measuring materials concentration when the device is attached to each calibrating element. In some embodiments, the illumination intensities may be affected by the optical characteristics of at least first layer 310 and second layer 320. The EM radiation reflected from second layer 320 may be affected by the ability of the material or materials in layer 320 (e.g., albumin and/or glucose) to absorb the EM radiation and the scattering, absorbing and reflecting properties of first layer 310. Processor 110 may receive from device 10, via communication unit 140 the sensed illumination intensities, sensed by sensor 210 for each calibrating element separately. Processor 110 may further receive information regarding form which calibrating element the illumination intensities was received and at which wavelength. In some embodiments, each calibrating element may be marked with a machine readable tag such as an RFID tag, a barcode or the like. In some embodiments, system 100 may further include a tag reader in communication with controller 110 that are configured to read an identification code included in the machine readable tag.

Accordingly, processor 110 may associate the received illumination intensities with the specific skin characteristics and the specific concentration of the calibrating element to which the device is attached, in operation 430.

An example for intensities (optical values) recorded for various calibrating elements at two wavelengths is given in table 1. The calibrating elements of table 1 includes at least two layers, a first layer simulating the skin thickness (2 mm for set 105 and 2.25 mm for set 106) and a second layer comprising albumin at concentrations of 3.5-3.7 g/dL.

TABLE 1

| | Wavelength of 1100 nm | | | Wavelength of 1290 nm | |
|---|---|---|---|---|---|
| element | Albumin concentration [g/dL] | Optical value [mW] | element | Albumin concentration [g/dL] | Optical value [mW] |
| Set 105 simulating skin thickness of 2 mm | | | Set 105 simulating skin thickness of 2 mm | | |
| 105a | 3.5 | 10 | 105a | 3.5 | 11 |
| 105b | 3.6 | 13 | 105b | 3.6 | 14 |
| 105c | 3.7 | 17 | 105c | 3.7 | 19 |
| Set 106 simulating skin thickness of 2.25 mm | | | Set 106 simulating skin thickness of 2.25 mm | | |
| 106a | 3.5 | 9 | 106a | 3.5 | 10 |
| 106b | 3.6 | 12 | 106b | 3.6 | 13 |
| 106c | 3.7 | 16 | 106c | 3.7 | 18 |

Processor 110 may form lookup tables, such as for example, table 1 and save the illumination intensities associated with the specific skin characteristics and the specific concentration in a memory (e.g., memory 250) of the device (e.g., device 10) for measuring materials concentration, in operation 440.

In some embodiments, some of the sets from the at least two sets of calibrating elements may include simulating a human skin with a first amount of color pigments and some of the sets from the at least two sets of calibrating elements includes simulating a human skin with a second amount of color pigments. In some embodiments, the received illumination intensities may include illumination intensities received from calibrating elements simulating a human skin with the first and second amount of color pigments. Accordingly, the lookup tables may further include illumination intensities associated with specific skin thickness having specific color (e.g., amount of pigment in the skin).

Accordingly, when device 10 is attached to a human's skin (e.g., human hand) with known skin thickness a reading from sensor 210 following illumination at a known wavelength may be accurately associated to a concentration of one or more materials (e.g., albumin and glucose) in the blood using the lookup tables stored in memory 250.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A system for calibrating a device for measuring materials concentration in blood, comprising:
   at least two sets of calibrating elements, each set comprising a plurality of calibrating elements,
      wherein each of the calibrating elements comprises:
      a first layer simulating a specific human skin characteristic; and
      a second layer comprising a specific concentration of one or more materials in the blood; and
      a third layer simulating illumination reflection from a blood vessel in a skin tissue,
   wherein the specific skin characteristics are selected from skin thickness, skin color, skin hair density, skin tone, an amount of pigment in the skin, skin optical properties and skin hair color;
   wherein in all calibrating elements in a set the first layer is the same first layer simulating the same human skin characteristics and each set of calibrating elements simulate different skin characteristics,
   wherein each calibrating element in a set of calibrating elements comprises a different second layer comprising a different concentration of the one or more materials;
   and wherein the third layer isolates the calibrating element from noise and reflections not related to the measured one or more materials in the second layer; and
   a controller configured to:
      receive illumination intensities from the device for measuring materials concentration when the device is attached to each calibrating element of the system;
      associate the received illumination intensities with the specific skin characteristics and the specific concentration of the calibrating element to which the device is attached; and
      save the illumination intensities associated with the specific skin characteristics and the specific concentration in lookup tables in memory of the device for measuring materials concentration.

2. The system of claim 1, wherein the received illumination intensities include illumination intensities at various wavelengths and wherein the saved lookup tables include lookup tables for illumination intensities of a specific wavelength associated with the specific skin characteristics, the one or more materials and the specific concentration.

3. A system for calibrating a device for measuring materials concentration in blood, comprising:
   a first set of calibrating elements;
   a second set of calibrating elements,
      wherein each of the calibrating elements in the first set and in the second set comprises:
      a first layer simulating a specific human skin characteristic;
      a second layer comprising a specific concentration of one or more materials in the blood; and
      a third layer simulating illumination reflection from a blood vessel in a skin tissue,
   wherein the specific skin characteristics are selected from skin thickness, skin color, skin hair density, skin tone, an amount of pigment in the skin, skin optical properties and skin hair color;
   wherein in the first set of calibrating elements the first layer simulates a first human skin characteristic and in the second set of calibrating elements the first layer simulates a second human skin characteristic, different from the first human skin characteristic, wherein each calibrating element in the first set comprises a different second layer comprising a different concentration of the one or more materials, and wherein each calibrating element in the second set comprises a different second layer comprising a different concentration of the one or more materials;

the third layer isolates the calibrating element from noise and reflections not related to the measured one or more materials in the second layer; and a controller configured to:

receive illumination intensities from the device for measuring materials concentration when the device is attached to each calibrating element of the system;

associate the received illumination intensities with the specific skin characteristic and the specific concentration of the measured one or more materials in the second layer of the calibrating element to which the device is attached; and save the illumination intensities associated with the specific skin thicknesses and the specific concentrations in a memory of the device for measuring materials concentration.

4. The system of claim 3, wherein the received illumination intensities include illumination intensities at various wavelengths and wherein the saved lookup tables include lookup tables for illumination intensities of a specific wavelength associated with the specific skin characteristics, the one or more materials and the specific concentration.

5. A method of calibrating a device for measuring materials concentration in blood, the method comprising:

attaching the device for measuring materials concentration to each calibrating element included in one of two or more sets of calibrating elements, wherein each of the calibrating elements comprises:

a first layer simulating a specific human skin characteristic;

a second layer comprising a specific concentration of one or more materials; and a third layer simulating illumination reflection from a blood vessel in a skin tissue, wherein the specific skin characteristics are selected from skin thickness, skin color, skin hair density, skin tone, an amount of pigment in the skin, skin optical properties and skin hair color;

wherein in all calibrating elements in a set the first layer is the same first layer simulating the same human skin characteristic and each set of calibrating elements simulate different skin characteristic, wherein each calibrating element in a set of calibrating elements comprises a different second layer comprising a different concentration of the one or more materials;

and wherein the third layer isolates the calibrating element from noise and reflections not related to the measured one or more materials in the second layer;

receiving, by a controller of a calibrating system, illumination intensities from the device for measuring materials concentration when the device is attached to each calibrating element;

associating, by the controller, the received illumination intensities with the specific skin characteristic and the specific concentration of the one or more materials in the second layer of the calibrating element to which the device is attached; and recording, by the controller, the illumination intensities associated with the specific skin characteristic and the specific concentrations in a memory of the device for measuring materials concentration.

6. The method of claim 5, wherein receiving illumination intensities includes receiving illumination intensities at various wavelengths and wherein recording the illumination intensities includes creating lookup tables for illumination intensities of a specific wavelength associated with the specific skin characteristic and the specific concentration.

* * * * *